United States Patent
Arunkumar et al.

(10) Patent No.: US 12,103,949 B2
(45) Date of Patent: Oct. 1, 2024

(54) PROTEIN RECOVERY

(71) Applicant: BRISTOL-MYERS SQUIBB COMPANY, Princeton, NJ (US)

(72) Inventors: Abhiram Arunkumar, Watertown, MA (US); Nripen Singh, Acton, MA (US); Ameya Umesh Borwankar, San Francisco, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 508 days.

(21) Appl. No.: 17/267,873

(22) PCT Filed: Aug. 13, 2019

(86) PCT No.: PCT/US2019/046250
§ 371 (c)(1),
(2) Date: Feb. 11, 2021

(87) PCT Pub. No.: WO2020/036903
PCT Pub. Date: Feb. 20, 2020

(65) Prior Publication Data
US 2021/0171573 A1 Jun. 10, 2021

Related U.S. Application Data (60) Provisional application No. 62/718,864, filed on Aug. 14, 2018.

(51) Int. Cl.
| | | |
|---|---|---|
| C07K 16/00 | (2006.01) | |
| C07K 1/34 | (2006.01) | |
| C07K 16/24 | (2006.01) | |
| C07K 16/28 | (2006.01) | |

(52) U.S. Cl.
CPC .............. *C07K 1/34* (2013.01); *C07K 16/244* (2013.01); *C07K 16/2803* (2013.01); *C07K 16/2866* (2013.01); *C07K 16/2878* (2013.01); *C07K 16/2896* (2013.01); *C07K 2319/30* (2013.01); *C07K 2319/31* (2013.01)

(58) Field of Classification Search
CPC .... C07K 1/34; C07K 16/244; C07K 16/2803; C07K 16/2878; C07K 16/2866; C07K 2319/30; C07K 16/2896; C07K 2319/31
See application file for complete search history.

(56) References Cited

U.S. PATENT DOCUMENTS

| | | |
|---|---|---|
| 2007/0237762 A1 | 10/2007 | Winter |
| 2008/0017576 A1 | 1/2008 | Belfort et al. |
| 2015/0360180 A1 | 12/2015 | Lutz et al. |

FOREIGN PATENT DOCUMENTS

| | | | |
|---|---|---|---|
| CN | 106565844 A | 4/2017 | |
| JP | H11512753 A | 11/1999 | |
| JP | 2012509658 A | 4/2012 | |
| JP | 2012521991 A | 9/2012 | |
| JP | 2013505029 A | 2/2013 | |
| JP | 2015517506 A | 6/2015 | |
| WO | WO9745140 | 12/1997 | |
| WO | 2009129226 A1 | 10/2009 | |
| WO | 2013031237 A1 | 3/2013 | |
| WO | WO-2017051273 A1 * | 3/2017 | ....... A61K 39/39591 |

OTHER PUBLICATIONS

Engineer Exel, https://engineerexcel.com/low-viscosity-liquids/#Low_Viscosity_Liquids, last visited Jun. 17, 2023.*
Bird et al, "Single-Chain Antigen-Binding Proteins", Science, vol. 242, 423-426.
Huston, James S., et al, Protein Engineering of Antibody Binding Sites: Recovery of Specific Activity in an Anti-Digoxin Single-Chain Fv Analogue Produced In *Escherichia coli*, Proc. Natl. Acad. Sci USA, 1988, 85, 5879-5883.
International Preliminary Report on Patentability for PCT/US2019/046250—Issued Feb. 25, 2021.
International Search Report for PCT/US2019/046250, Filed: Aug. 13, 2019.
Ward, E. Sally, et al, "Binding Activities of a Repertoire of Single Immunoglobulin Variable Domains Secreted From *Escherichia coli*", Letters to Nature, 341: 544-546.

* cited by examiner

*Primary Examiner* — Jeanette M Lieb
(74) *Attorney, Agent, or Firm* — Sterne, Kessler, Goldstein & Fox P.L.L.C.

(57) ABSTRACT

This disclosure provides a novel flush method using a recovery flush technique that minimizes yield losses due to inadequate flushing and prevents or reduces dilution of a target protein during a recovery flush.

35 Claims, 2 Drawing Sheets

PROTEIN RECOVERY

REFERENCE TO RELATED APPLICATIONS

This application is a 371 application of PCT/US2019/046250, filed Aug. 13, 2019, which claims benefit to U.S. provisional patent application No. 62/718,864, Aug. 14, 2018, the contents of each of which are hereby incorporated herein by reference in their entirety.

BACKGROUND OF THE DISCLOSURE

Subcutaneous delivery of a variety of therapeutic proteins is a fast-growing field, especially for specific protein subtypes such as monoclonal antibodies, which require large quantities of drug to be administered. In order to properly formulate these molecules, a concentration of greater than 100 g/L is required. Both the manufacture of these molecules at these high concentrations and the large-scale recovery of highly concentrated products at scale using tangential flow filtration (TFF) or other filtration methods are known to be difficult.

Tangential flow filtration (TFF) is a rapid and efficient method for separation and purification of biomolecules. It can be applied to a wide range of biological fields such as immunology, protein chemistry, molecular biology, biochemistry, and microbiology. TFF can be used to concentrate and desalt sample solutions ranging in volume from 10 mL to thousands of liters, and can be used to fractionate large from small biomolecules, harvest cell suspensions, and clarify fermentation broths and cell lysates. Membrane filtration is a separation technique widely used in the life science laboratory. Depending on membrane porosity, it can be classified as a microfiltration or ultrafiltration process. Ultrafiltration membranes, with pore sizes generally between 0.001 and 0.1 μm, are used for concentrating and desalting dissolved molecules (proteins, peptides, nucleic acids, carbohydrates, and other biomolecules), exchanging buffers, and gross fractionation. Ultrafiltration membranes are typically classified by molecular weight cutoff (MWCO) rather than pore size.

It is well known that during high viscosity ultrafiltration at high protein concentrations intended at the drug substance stage (>150 mg/mL), the burden of achieving the target concentration comes upon the ultrafiltration/diafiltration (UF/DF) process. One issue encountered in manufacturing is retention of protein in the manufacturing tubing or other "hold-up" areas, leading to poor recovery in the collection vessel and therefore poor yield. Thus, the typical practice has been to employ a recovery flush to push the retained protein into the collection vessel to increase overall yield. If the flush behavior followed ideal plug flow conditions, there would be no dilution during the flush and instead the flush buffer would simply push the protein into the collection vessel and take its place in the "hold-up" areas, and recovery of protein trapped in the "hold-up" areas without dilution would not be a problem. However under real-world conditions, the recovery flush causes dilution of the product because dilution occurs between the recovery flush buffer and the protein to be pushed into the collection vessel. Therefore, there is a need to reduce or prevent dilution of a target product during a recovery flush.

SUMMARY OF THE DISCLOSURE

The present disclosure is related to a method of reducing or preventing dilution of a target protein during a recovery flush after a filtration. One aspect of the present disclosure is directed to (i) passing a sample containing the target protein through a filtration assembly at a feed flow rate while the filtration is on and (ii) passing a buffer through the filtration assembly during a recovery flush at a flush flow rate that is less than 100 liters per square meter per hour (LMH), thereby reducing or preventing dilution of the target protein compared to the dilution of a target protein obtained with a flush flow rate of 300 LMH. In another aspect, the present disclosure is related to a method of improving or increasing a concentration of a target protein during a recovery flush after a filtration. One aspect of the present disclosure is directed to (i) passing a sample containing the target protein through a filtration assembly at a feed flow rate while the filtration is on and (ii) passing a flush buffer through the filtration assembly during a recovery flush at a flush flow rate that is less than 100 liters per square meter per hour (LMH), thereby improving the target protein concentration compared to a target protein concentration obtained with a flush flow rate of 300 LMH.

In some embodiments, the Reynold's number ("Re") of the flow in the recovery flush is less than 2000, less than 1500, less than 1000, less than 900, less than 800, less than 700, less than 600, less than 500, less than 400, less than 300, less than 200, less than 100, less than 90, less than 80, less than 70, less than 60, less than 50, less than 40, less than 30, less than 20, less than 10, less than 5, less than 4, or less than 3, wherein the Re is calculated with the following formula:

$$Re = D\upsilon\rho/\mu, \text{ and}$$

wherein D is the diameter of the channel (m) or equivalent diameter in the case of non-cylindrical flow channel geometries, $\upsilon$ is average velocity (m/s) ($Q/A_c$), $\rho$ is density (kg/m$^3$), and $\mu$ is the viscosity (Pa·s).

In some embodiments, the Reynold's number (Re) of the flow in the recovery flush is between about 1 and about 50, between about 1 and about 45, between about 1 and about 40, between about 1 and about 35, between about 1 and about 30, between about 1 and about 25, between about 1 and about 20, between about 1 and about 15, between about 1 and about 10, between about 2 and about 40, between about 1 and about 10, between about 2 and about 9, between about 3 and about 8, between about 4 and about 7, between about 4 and about 6, between about 3 and about 7, between about 3 and about 6, between about 3 and about 5, between about 2 and about 8, between about 2 and about 7, between about 2 and about 6, between about 2 and about 5, between about 3 and about 10, or between about 4 and about 6.

In some embodiments, the Reynold's number (Re) of the flow in the recovery flush is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30. In some embodiments the Re of the flow in the recovery flush is about 3.8.

In some embodiments, the flush flow rate is between about 5 LMH and about 100 LMH, between about 10 LMH and about 100 LMH, between about 10 LMH and about 90 LMH, between about 10 LMH and about 80 LMH, between about 10 LMH and about 70 LMH, between about 10 LMH and about 60 LMH, between about 10 LMH and about 50 LMH, between about 10 LMH and about 40 LMH, between about 10 LMH and about 30 LMH, between about 30 LMH and about 50 LMH, between about 20 LMH and about 100 LMH, between about 20 LMH and about 90 LMH between about 20 LMH and about 80 LMH, between about 20 LMH and about 70 LMH, between about 20 LMH and about 60 LMH, between about 20 LMH and about 50 LMH, between about 20 LMH and about 40 LMH, between about 30 LMH and about 100 LMH, between about 30 LMH and about 90 LMH, between about 30 LMH and about 80 LMH, between about 30 LMH and about 70 LMH, between about 30 LMH and about 60 LMH, between about 30 LMH and about 50 LMH, between about 30 LMH and about 40 LMH, or between about 20 LMH and about 30 LMH.

In some embodiments, the flush flow rate is at least about 10 LMH, at least about 20 LMH, at least about 30 LMH, at least about 40 LMH, at least about 50 LMH, at least about 60 LMH, at least about 70 LMH, at least about 80 LMH, at least about 90 LMH or at least about 100 LMH. In some embodiments, the flush flow rate is about 30 LMH.

The present methods can be especially effective during high viscosity ultrafiltration at high protein concentrations intended at the drug substance stage (>150 mg/mL). In some embodiments, the viscosity of the target protein is at least about 1 centipoise (cP), at least about 2 cP, at least about 3 cP, at least about 4 cP, at least about 5 cP, at least about 6 cP, at least about 7 cP, at least about 8 cP, at least about 9 cP, at least about 10 cP, at least about 11 cP, at least about 12 cP, at least about 13 cP, at least about 14 cP, at least about 15 cP, at least about 16 cP, at least about 17 cP, at least about 18 cP, at least about 19 cP, at least about 20 cP, at least about 21 cP, at least about 22 cP, at least about 23 cP, at least about 24 cP, at least about 25 cP, at least about 26 cP, at least about 27 cP, at least about 28 cP, at least about 29 cP, or at least about 30 cP.

In some embodiments, the viscosity of the target protein is high, and is at least about 20 centipoise (cP), at least about 21 cP, at least about 22 cP, at least about 23 cP, at least about 24 cP, at least about 25 cP, at least about 26 cP, at least about 27 cP, at least about 28 cP, at least about 29 cP, at least about 30 cP, at least about 31 cP, at least about 32 cP, at least about 33 cP, at least about 34 cP, at least about 35 cP, at least about 36 cP, at least about 37 cP, at least about 38 cP, at least about 39 cP, at least about 40 cP, at least about 41 cP, at least about 42 cP, at least about 43 cP, at least about 44 cP, at least about 45 cP, at least about 46 cP, at least about 47 cP, at least about 48 cP, at least about 49 cP, at least about 50 cP, at least about 51 cP, at least about 52 cP, at least about 53 cP, at least about 54 cP, at least about 55 cP, at least about 56 cP, at least about 57 cP, at least about 58 cP, at least about 59 cP, at least about 60 cP, at least about 61 cP, at least about 62 cP, at least about 63 cP, at least about 64 cP, at least about 65 cP, at least about 66 cP, at least about 67 cP, at least about 68 cP, at least about 69 cP, at least about 70 cP, at least about 71 cP, at least about 72 cP, at least about 73 cP, at least about 74 cP, at least about 75 cP, at least about 76 cP, at least about 77 cP, at least about 78 cP, at least about 79 cP, at least about 80 cP, at least about 81 cP, at least about 82 cP, at least about 83 cP, at least about 84 cP, at least about 85 cP, at least about 86 cP, at least about 87 cP, at least about 88 cP, at least about 89 cP, at least about 90 cP, at least about 91 cP, at least about 92 cP, at least about 93 cP, at least about 94 cP, at least about 95 cP, at least about 96 cP, at least about 97 cP, at least about 98 cP, at least about 99 cP, or at least about 100 cP.

In some embodiments, the viscosity of the target protein is from about 2 cP to about 10 cP, from about 3 cP to about 10 cP, from about 1 cP to about 9 cP, from about 2 cP to about 8 cP, from about 2 cP to about 7 cP, from about 2 cP to about 6 cP, from about 3 cP to about 6 cP, from about 4 cP to about 5 cP, or from about 2 cP to about 5 cP.

In some embodiments, the concentration of the target protein after the recovery flush is at least about 100 g/L, at least about 110 g/L, at least about 120 g/L, at least about 130 g/L, at least about 140 g/L, at least about 150 g/L, at least about 160 g/L, at least about 170 g/L, at least about 180 g/L, at least about 190 g/L, at least about 200 g/L, at least about 210 g/L, at least about 220 g/L, at least about 230 g/L, at least about 240 g/L, at least about 250 g/L, at least about 260 g/L, at least about 270 g/L, at least about 280 g/L, at least about 290 g/L, or at least about 300 g/L before the filtrations.

In some embodiments, the concentration of the target protein after the recovery flush is from about 100 g/L to about 300 g/L, from about 110 g/L to about 250 g/L, from about 120 g/L to about 240 g/L, from about 150 g/L to about 250 g/L, from about 130 g/L to about 260 g/L, from about 140 g/L to about 260 g/L, from about 160 g/L to about 220 g/L, or from about 170 g/L to about 230 g/L.

In some embodiments, the concentration of the target protein after the recovery flush is about 90 g/L, about 100 g/L, about 110 g/L, about 120 g/L, about 130 g/L, about 140 g/L, about 150 g/L, about 160 g/L, about 170 g/L, about 180 g/L, about 190 g/L, about 200 g/L, about 210 g/L, about 220 g/L, about 230 g/L, about 240 g/L, about 250 g/L, about 260 g/L, about 270 g/L, about 280 g/L, about 290 g/L, or about 300 g/L.

The present methods thereby can result in the increased protein yield after the recovery flush by preventing or reducing dilution of the target protein during the recovery flush. In some embodiments, the yield of the target protein after the recovery flush is at least 90%, at least 91%, at least 92%, at least 93%, at least 94%, at least 95%, at least 96%, at least 97%, at least 98%, at least 99%, or at least 100% compared to the concentration of the target protein prior to the recovery flush process consisting of (i) passing a sample containing the target protein through a filtration assembly at a feed flow rate while the filtration is on and (ii) passing a buffer through the filtration assembly during a recovery flush at a flush flow rate that is less than 100 liters per square meter per hour (LMH).

In some embodiments, the yield of the target protein after the recovery flush is increased by at least 1%, at least 2%, at least 3%, at least 5%, at least 10%, at least 15%, or at least 20% compared to a yield of the target protein obtained after a recovery flush with a flow rate of 300 LMH. In some embodiments, the passing in (i) is at a feed flow rate higher than the flush flow rate in (ii).

In some embodiments, the feed flow rate is at least 200 LMH, at least 210 LMH, at least 220 LMH, at least 230 LMH, at least 240 LMH, at least 250 LMH, at least 260 LMH, at least 270 LMH, at least 280 LMH, at least 290 LMH, at least 300 LMH, at least 310 LMH, at least 320 LMH, at least 330 LMH, at least 340 LMH, at least 350 LMH, at least 360 LMH, at least 370 LMH, at least 380 LMH, at least 390 LMH, at least 400 LMH, at least 410 LMH, at least 420 LMH, at least 430 LMH, at least 440 LMH, at least 450 LMH, at least 460 LMH, at least 470 LMH, at least 480 LMH, at least 490 LMH, or at least 500 LMH.

In some embodiments, the feed flow rate is between 200 LMH and 500 LMH, between 200 LMH and 450 LMH, between 250 LMH and 450 LMH, 450 LMH, between 300 LMH and 450 LMH, between 300 LMH and 400 LMH, or between 300 LMH and 350 LMH. In some embodiments, the feed flow rate is about 300 LMH.

In some embodiments, the filtration assembly comprises a membrane. In some embodiments, the filtration membrane useful for the filtration assembly is derived from polyvinylidene fluoride (PVDF), polysulfone, polyethersulfone, polyarylsulfone, regenerated cellulose, polyamide, polypropylene, polyethylene, polytetrafluoroethylene, cellulose acetate, polyacrylonitrile, vinyl copolymer, polyamides (such as "Nylon 6" or Nylon 66") polycarbonate, PFA, or any combination thereof. In some embodiments, the flush buffer comprises an organic or inorganic acid or salt thereof.

In some embodiments, the organic or inorganic acid is citrate (e.g., monosodium citrate-disodium citrate mixture, citric acid-trisodium citrate mixture, citric acid-monosodium citrate mixture, etc.), succinate (e.g., succinic acid-monosodium succinate mixture, succinic acid-sodium hydroxide mixture, succinic acid-disodium succinate mixture, etc.), tartrate (e.g., tartaric acid-sodium tartrate mixture, tartaric acid-potassium tartrate mixture, tartaric acid-sodium hydroxide mixture, etc.), fumarate (e.g., fumaric acid-monosodium fumarate mixture, fumaric acid-disodium fumarate mixture, monosodium fumarate-disodium fumarate mixture, etc.), gluconate (e.g., gluconic acid-sodium glyconate mixture, gluconic acid-sodium hydroxide mixture, gluconic acid-potassium glyuconate mixture, etc.), oxalate (e.g., oxalic acid-sodium oxalate mixture, oxalic acid-sodium hydroxide mixture, oxalic acid-potassium oxalate mixture, etc.), lactate (e.g., lactic acid-sodium lactate mixture, lactic acid-sodium hydroxide mixture, lactic acid-potassium lactate mixture, etc.) acetate (e.g., acetic acid-sodium acetate mixture, acetic acid-sodium hydroxide mixture, etc.), trimethylamine salt (e.g., Tris), phosphate, or histidine. In some embodiments, the flush buffer comprises histidine. In some embodiments, the flush buffer comprises a sugar. In some embodiments, the sugar is sucrose, trehalose, mannitol, xylitol, erythritol, lactose, glucose, powdered sugar, or pullulan. In some embodiments, the flush buffer comprises 20 mM histidine and 250 mM sucrose.

In some embodiments, a filtration buffer is used during (i). In some embodiments, the filtration buffer is the same as the flush buffer. In other embodiments, the filtration buffer is different from the flush buffer. In some embodiments, the filtration buffer comprises an organic and inorganic acid or salt thereof.

In some embodiments, the organic or inorganic acid is citrate (e.g., monosodium citrate-disodium citrate mixture, citric acid-trisodium citrate mixture, citric acid-monosodium citrate mixture, etc.), succinate (e.g., succinic acid-monosodium succinate mixture, succinic acid-sodium hydroxide mixture, succinic acid-disodium succinate mixture, etc.), tartrate (e.g., tartaric acid-sodium tartrate mixture, tartaric acid-potassium tartrate mixture, tartaric acid-sodium hydroxide mixture, etc.), fumarate (e.g., fumaric acid-monosodium fumarate mixture, fumaric acid-disodium fumarate mixture, monosodium fumarate-disodium fumarate mixture, etc.), gluconate (e.g., gluconic acid-sodium glyconate mixture, gluconic acid-sodium hydroxide mixture, gluconic acid-potassium glyuconate mixture, etc.), oxalate (e.g., oxalic acid-sodium oxalate mixture, oxalic acid-sodium hydroxide mixture, oxalic acid-potassium oxalate mixture, etc.), lactate (e.g., lactic acid-sodium lactate mixture, lactic acid-sodium hydroxide mixture, lactic acid-potassium lactate mixture, etc.) acetate (e.g., acetic acid-sodium acetate mixture, acetic acid-sodium hydroxide mixture, etc.), trimethylamine salt (e.g., Tris), phosphate, or histidine.

In some embodiments, the filtration buffer comprises a sugar. In some embodiments, the sugar is sucrose, trehalose, mannitol, xylitol, erythritol, lactose, glucose, powdered sugar, or pullulan. In some embodiments, the flush buffer and/or the filtration buffer is at a pH of about 4, about 4.5, about 5, about 5.5, about 6, about 6.5, about 7, about 7.5, about 8, about 8.5, about 9, or about 9.5.

In some embodiments, the sample is selected from the group consisting of a pure protein sample, a clarified bulk protein sample, a cell culture sample, and any combination thereof. In some embodiments, the cell culture sample is derived from cell culture media comprising mammalian cells. In some embodiments, the mammalian cells are selected from Chinese hamster ovary (CHO) cells, HEK293 cells, mouse myeloma (NS0), baby hamster kidney cells (BHK), monkey kidney fibroblast cells (COS-7), Madin-Darby bovine kidney cells (MDBK) or any combination thereof.

In some embodiments, the target protein comprises an antibody or a fusion protein. In some embodiments, the target protein comprises an antibody. In some embodiments, the antibody is an isotype selected from IgM, IgA, IgE, IgD, and IgG. In some embodiments, the IgG antibody is selected from IgG1, IgG2, IgG3, and IgG4. In some embodiments, the antibody is an anti-GITR antibody, an anti-CXCR4 antibody, an anti-CD73 antibody, an anti-TIGIT antibody, an anti-OX40 antibody, an anti-LAG3 antibody, an anti-CSF1R antibody, or an anti-IL8 antibody.

In some embodiments, the target protein comprises an enzyme, a hormone, a cytokine, a cell surface receptor, a protease, a cytokine receptor, or any combination thereof. In some embodiments, the target protein is a fusion protein. In some embodiments, the fusion protein is fused to a heterologous moiety. In some embodiments, the heterologous moiety is a half-life extending moiety. In some embodiments, the half-life extending moiety comprises an Fc.

DETAILED DESCRIPTION OF THE DISCLOSURE

The present disclosure provides a highly effective approach to reducing or preventing the dilution of a target protein during a recovery flush. Specifically, the approach uses slower flow-rates to combat the dilution effects of turbulent flow that occurs when the calculated Reynold's Number (Re) is high. In some embodiments, the calculated Re useful for the present methods is lower than 2000.

As shown in the working examples, the approach is effective at reducing or preventing the dilution of a target protein during a recovery flush caused by the recovery flush flow-rate. In certain embodiments, the present disclosure provides a method of reducing or preventing dilution of a target protein during a recovery flush by using a recovery flush flow-rate of 30 LMH, thereby reducing or preventing dilution of the target protein compared to the dilution of a target protein obtained with a recovery flush flow-rate of 100 LMH. Use of such a system allows for very minimal dilution of a target protein during a recovery flush, which allows for a higher final target concentration to be reached without sacrificing product yield or concentration, either due to the absence of a recovery flush or excessive dilution due to a faster recovery flush-flow rate.

In certain embodiments, the present disclosure provides a method of purifying a protein of interest from a mixture which comprises the protein of interest and one or more contaminants. Possible contaminants include host cell proteins (HCP), high molecular weight species (HMWs), low molecular weight species (LMWs), or DNA.

In certain embodiments, the present disclosure provides a method of purifying an antibody. In certain embodiments, the mixture is derived from harvested cell culture fluid, cell culture supernatant, cell lysate, and clarified bulk.

I. Terms

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

As used herein, the term "protein of interest" is used in its broadest sense to include any protein (either natural or recombinant), present in a mixture, for which purification is desired. Such proteins of interest include, without limitation, enzymes, hormones, growth factors, cytokines, immunoglobulins (e.g., antibodies), and/or any fusion proteins.

The term "clarification" refers to the process of removing particulates. Clarification can lower the burden on subsequent chromatography (for example, AEX or CEX) during a purification process. In some examples, clarification is a method of removing colloids, lipids, DNA-RNA, residual cells, and other particles from cell culture. Filtration may also be used, and can include depth filters. "Clarified bulk" refers to a mixture that has been subjected to the process of clarification.

The term "virus inactivation" refers to a process of removing infective viral contaminants from a mixture. There are currently many different methods for inactivating contagious pathogenic viruses, including, e.g., heat-inactivation, solvent/detergent (S/D) inactivation, pH inactivation, chemical inactivation, and/or ultraviolet irradiation inactivation.

The term "chromatography" refers to any kind of technique which separates a protein of interest (e.g., an antibody) from other molecules (e.g., contaminants) present in a mixture. Usually, the protein of interest is separated from other molecules (e.g., contaminants) as a result of differences in rates at which the individual molecules of the mixture migrate through a stationary medium under the influence of a moving phase, or in bind and elute processes. The term "matrix" or "chromatography matrix" are used interchangeably herein and refer to any kind of sorbent, resin or solid phase which in a separation process separates a protein of interest (e.g., an Fc region containing protein such as an immunoglobulin) from other molecules present in a mixture. Non-limiting examples include particulate, monolithic or fibrous resins as well as membranes that can be put in columns or cartridges. Examples of materials for forming the matrix include polysaccharides (such as agarose and cellulose); and other mechanically stable matrices such as silica (e.g. controlled pore glass), poly(styrenedivinyl)benzene, polyacrylamide, ceramic particles and derivatives of any of the above. Examples for typical matrix types suitable for the method of the present disclosure are cation exchange resins, affinity resins, anion exchange resins or mixed mode resins. A "ligand" is a functional group that is attached to the chromatography matrix and that determines the binding properties of the matrix. Examples of "ligands" include, but are not limited to, ion exchange groups, hydrophobic interaction groups, hydrophilic interaction groups, thiophilic interactions groups, metal affinity groups, affinity groups, bioaffinity groups, and mixed mode groups (combinations of the aforementioned). Some preferred ligands that can be used herein include, but are not limited to, strong cation exchange groups, such as sulphopropyl, sulfonic acid; strong anion exchange groups, such as trimethylammonium chloride; weak cation exchange groups, such as carboxylic acid; weak anion exchange groups, such as N5N diethylamino or DEAE; hydrophobic interaction groups, such as phenyl, butyl, propyl, hexyl; and affinity groups, such as Protein A, Protein G, and Protein L. In order that the present disclosure may be more readily understood, certain terms are first defined. As used in this application, except as otherwise expressly provided herein, each of the following terms shall have the meaning set forth below. Additional definitions are set forth throughout the application.

The term "affinity chromatography" refers to a protein separation technique in which a protein of interest (e.g., an Fc region containing protein of interest or antibody) is specifically bound to a ligand which is specific for the protein of interest. Such a ligand is generally referred to as a biospecific ligand. In some embodiments, the biospecific ligand (e.g., Protein A or a functional variant thereof) is covalently attached to a chromatography matrix material and is accessible to the protein of interest in solution as the solution contacts the chromatography matrix. The protein of interest generally retains its specific binding affinity for the biospecific ligand during the chromatographic steps, while other solutes and/or proteins in the mixture do not bind appreciably or specifically to the ligand. Binding of the protein of interest to the immobilized ligand allows contaminating proteins or protein impurities to be passed through the chromatography matrix while the protein of interest remains specifically bound to the immobilized ligand on the solid phase material. The specifically bound protein of interest is then removed in active form from the immobilized ligand under suitable conditions (e.g., low pH, high pH, high salt, competing ligand etc.), and passed through the chromatographic column with the elution buffer, free of the contaminating proteins or protein impurities that were earlier allowed to pass through the column. Any component can be used as a ligand for purifying its respective specific binding protein, e.g., antibody. However, in various methods according to the present disclosure, Protein A is used as a ligand for an Fc region containing a target protein. The conditions for elution from the biospecific ligand (e.g., Protein A) of the target protein (e.g., an Fc region containing protein) can be readily determined by one of ordinary skill in the art. In some embodiments, Protein G or Protein L or a functional variant thereof may be used as a biospecific ligand. In some embodiments, a biospecific ligand such as Protein A is used at a pH range of 5-9 for binding to an Fc region containing protein, washing or re-equilibrating the biospecific ligand/target protein conjugate, followed by elution with a buffer having pH about or below 4 which contains at least one salt.

The terms "purifying," "separating," or "isolating," as used interchangeably herein, refer to increasing the degree of purity of a protein of interest from a composition or sample comprising the protein of interest and one or more impurities. Typically, the degree of purity of the protein of interest is increased by removing (completely or partially) at least one impurity from the composition.

The term "buffer" as used herein, refers to a substance which, by its presence in solution, increases the amount of acid or alkali that must be added to cause unit change in pH. A buffered solution resists changes in pH by the action of its acid-base conjugate components. Buffered solutions for use with biological reagents are generally capable of maintaining a constant concentration of hydrogen ions such that the pH of the solution is within a physiological range. Traditional buffer components include, but are not limited to, organic and inorganic salts, acids and bases.

The term "chromatography column" or "column" in connection with chromatography as used herein, refers to a container, frequently in the form of a cylinder or a hollow pillar which is filled with the chromatography matrix or resin. The chromatography matrix or resin is the material which provides the physical and/or chemical properties that are employed for purification.

The terms "ion-exchange" and "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange (CEX), anion exchange (AEX), and mixed mode chromatography.

As used herein the term "contaminant" is used in its broadest sense to cover any undesired component or compound within a mixture. In cell cultures, cell lysates, or clarified bulk (e.g., clarified cell culture supernatant), contaminants include, for example, host cell nucleic acids (e.g., DNA) and host cell proteins present in a cell culture medium. Host cell contaminant proteins include, without limitation, those naturally or recombinantly produced by the host cell, as well as proteins related to or derived from the protein of interest (e.g., proteolytic fragments) and other process related contaminants. In certain embodiments, the contaminant precipitate is separated from the cell culture using a means such as centrifugation, sterile filtration, depth filtration and tangential flow filtration.

The term "Reynolds Number" (Re) is calculated with the following formula:

$$Re = D\upsilon\rho/\mu, \text{ and}$$

wherein D is the diameter of the channel (m) or equivalent diameter in the case of non-cylindrical flow channel geometries, $\upsilon$ is average velocity (m/s) (Q/Ac), $\rho$ is density (kg/m$^3$), and $\mu$ is the viscosity (PA s). A Reynolds Number is a dimensionless unit and describes the ratio of inertial forces to viscous forces in a flowing fluid. It is used in many fluid flow correlations and is used to describe the boundaries of fluid flow regimes (laminar, transitional and turbulent). Laminar flow occurs when a fluid flows in parallel layers, with no disruption between layers. When the Reynolds number is less than about 2,000, flow in a tube is generally laminar. When the Reynolds number is greater than about 4,000, the flow is turbulent. A Reynolds number between 2,000 and 4,000 represents an area of transition between laminar flow and turbulent flow.

The term "recovery flush" refers to a protein purification step where a protein sample that has already been concentrated above its desired target concentration is subjected to a flush to displace additional protein that has not yet reached the collection vessel. The amount of overconcentration in the overconcentration step influences the flush volume that can be used in the recovery step, because it determines the amount of dilution possible before reaching the final target protein concentration. In many protein purification processes at scale, a significant amount of protein can be held outside of the collection vessels in the tubing, piping or other "hold-up" areas, and a recovery flush is necessary to recover a larger amount of protein product in the collection vessel or other container used to collect the purified protein product. In the absence of a recovery flush, protein product that has accumulated in the tubing, piping, or other "hold-up" areas of the large-scale protein purification system may otherwise be lost or not recovered due to its failure to reach the protein collection vessel or other container used to collect the purified protein product.

The term "flush buffer" refers to the solution or mixture used during the recovery flush which is used to either increase overall protein yield, dilute the protein to its final target concentration, or both. The flush buffer is also used to push the protein out of the tubing or other areas of the filtration assembly where protein accumulates.

The term "filtration buffer" refers to the solution or mixture used during filtration which is used to pass a feed containing a protein of interest over or through a membrane.

The term "filtration assembly" refers to the entire system used to perform protein purification. One example of a filtration assembly is a tangential flow filtration (TFF) system where a feed containing a protein of interest is subjected to a feed flow that is perpendicular to a filtration membrane. Commercially available TFF systems include the AKTA® Flux Tangential Flow Filtration System (GE Life Sciences). Another example of a filtration assembly is a direct flow filtration (DFF) system where a feed containing a protein of interest is subjected to a feed flow that is parallel to a filtration membrane.

The term "feed flow rate" (LMH), or sometimes "crossflow rate" refers to a rate of flow in a step in tangential flow filtration (TFF) protein purification wherein a feed containing a protein of interest is subjected to a feed flow that is perpendicular to a filtration membrane. The tangential flow of the feed prevents particles trapped on the surface of the filter to accumulate and therefore interfere with filtration. During an ultrafiltration concentration step, the feed flow to the ultrafiltration membrane cassette provides the necessary transmembrane pressure (TMP) and crossflow flux for the concentration and buffer exchange. In the context of Direct Flow Filtration (DFF) systems, the term "feed flow rate" refers to a rate of flow that is parallel to a filtration membrane.

The term "flush flow rate" (LMH) refers to a flow rate used in a protein purification step where a protein sample that has already been concentrated above its desired target concentration is subjected to a flush to displace the protein not present in the collection vessel. The flush flow rate represents the rate at which a flush buffer flows through the system during the recovery flush phase of the purification process.

The term "diafiltration" refers to the process of removing, replacing, or lowering the concentration of salts or solvents from solutions containing proteins, peptides, nucleic acids, and other biomolecules. The process uses permeable membrane filters to separate the components of a solution or mixture based on molecular size. Molecules that are smaller than the pores of the membrane freely pass through the membrane.

The term "ultrafiltration" refers to the process of the separation of particles of one size from particles of another size using a filter. Ultrafiltration is a pressure-driven membrane process that is widely used for protein concentration and buffer exchange. Ultrafiltration is a size-based separation, where species larger than the membrane pores are retained and smaller species pass through the filter. Ultrafiltration is done through differences in the filtration rates of different components across the membrane under pressure.

The term "antibody" refers, in some embodiments, to a protein comprising at least two heavy (H) chains and two light (L) chains inter-connected by disulfide bonds. Each heavy chain is comprised of a heavy chain variable region (abbreviated herein as VH) and a heavy chain constant region (abbreviated herein as CH). In some antibodies, e.g., naturally-occurring IgG antibodies, the heavy chain constant region is comprised of a hinge and three domains, CH1, CH2 and CH3. In some antibodies, e.g., naturally-occurring IgG antibodies, each light chain is comprised of a light chain variable region (abbreviated herein as VL) and a light chain constant region. The light chain constant region is comprised of one domain (abbreviated herein as CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. A heavy chain may have the C-terminal lysine or not. The term "antibody" can include a bispecific antibody or a multispecific antibody.

An "IgG antibody", e.g., a human IgG1, IgG2, IgG3 and IgG4 antibody, as used herein has, in some embodiments, the structure of a naturally-occurring IgG antibody, i.e., it has the same number of heavy and light chains and disulfide bonds as a naturally-occurring IgG antibody of the same subclass. For example, an IgG1, IgG2, IgG3 or IgG4 antibody may consist of two heavy chains (HCs) and two light chains (LCs), wherein the two HCs and LCs are linked by the same number and location of disulfide bridges that occur in naturally-occurring IgG1, IgG2, IgG3 and IgG4 antibodies, respectively (unless the antibody has been mutated to modify the disulfide bridges).

An immunoglobulin can be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., IgG1, exist in several allotypes, which differ from each other in at most a few amino acids. "Antibody" includes, by way of example, both naturally-occurring and non-naturally-occurring antibodies; monoclonal and polyclonal antibodies; chimeric and humanized antibodies; human and nonhuman antibodies and wholly synthetic antibodies.

The term "antigen-binding portion" of an antibody, as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment (fragment from papain cleavage) or a similar monovalent fragment consisting of the VL, VH, LC and CH1 domains; (ii) a F(ab')2 fragment (fragment from pepsin cleavage) or a similar bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; (vi) an isolated complementarity determining region (CDR) and (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

An "Fc region" (fragment crystallizable region), "Fc domain," or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. The IgG isotype is divided in subclasses in certain species: IgG1, IgG2, IgG3 and IgG4 in humans, and IgG1, IgG2a, IgG2b and IgG3 in mice. For IgG, the Fc region comprises immunoglobulin domains CH2 and CH3 and the hinge between CH1 and CH2 domains. Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3 and P224 for IgG4 to the carboxy-terminus of the heavy chain, wherein the numbering is according to the EU index as in Kabat. The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally-occurring Fc).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are known in the art. The majority of innate effector cell types co-express one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

As used herein, the term "polypeptide" refers to a molecule composed of monomers (amino acids) linearly linked by amide bonds (also known as peptide bonds). The term "polypeptide" refers to any chain or chains of two or more amino acids, and does not refer to a specific length of the product. As used herein the term "protein" is intended to encompass a molecule comprised of one or more polypeptides, which can in some instances be associated by bonds other than amide bonds. On the other hand, a protein can also be a single polypeptide chain. In this latter instance the single polypeptide chain can in some instances comprise two or more polypeptide subunits fused together to form a protein. The terms "polypeptide" and "protein" also refer to the products of post-expression modifications, including without limitation glycosylation, acetylation, phosphorylation, amidation, derivatization by known protecting/blocking groups, proteolytic cleavage, or modification by non-naturally occurring amino acids. A polypeptide or protein can be derived from a natural biological source or produced by recombinant technology, but is not necessarily translated from a designated nucleic acid sequence. It can be generated in any manner, including by chemical synthesis.

The terms "polynucleotide" or "nucleotide" as used herein are intended to encompass a singular nucleic acid as well as plural nucleic acids, and refers to an isolated nucleic acid molecule or construct, e.g., messenger RNA (mRNA), complementary DNA (cDNA), or plasmid DNA (pDNA). In certain aspects, a polynucleotide comprises a conventional phosphodiester bond or a non-conventional bond (e.g., an amide bond, such as found in peptide nucleic acids (PNA)).

The term "nucleic acid" refers to any one or more nucleic acid segments, e.g., DNA, cDNA, or RNA fragments, present in a polynucleotide. When applied to a nucleic acid or polynucleotide, the term "isolated" refers to a nucleic acid molecule, DNA or RNA, which has been removed from its native environment, for example, a recombinant polynucleotide encoding an antigen binding protein contained in a vector is considered isolated for the purposes of the present disclosure. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present disclosure. Isolated polynucleotides or nucleic acids according to the present disclosure further include such molecules produced synthetically. In addition, a polynucleotide or a nucleic acid can include regulatory elements such as promoters, enhancers, ribosome binding sites, or transcription termination signals.

Ranges: As described herein, any concentration range, percentage range, ratio range or integer range is to be understood to include the value of any integer within the recited range and, when appropriate, fractions thereof (such as one tenth and one hundredth of an integer), unless otherwise indicated.

The term "HMW Species" refers to any one or more unwanted proteins present in a mixture. High molecular weight species can include dimers, trimers, tetramers, or other multimers. These species are often considered product related impurities, and can either be covalently or non-covalently linked, and can also, for example, consist of misfolded monomers in which hydrophobic amino acid residues are exposed to a polar solvent, and can cause aggregation.

The term "LMW Species" refers to any one or more unwanted species present in a mixture. Low molecular weight species are often considered product related impurities, and can include clipped species, or half molecules for compounds intended to be dimeric (such as monoclonal antibodies).

The term "Host Cell Proteins" or HCP refers to the undesirable proteins generated by a host cell unrelated to the production of the intended protein of interest. Undesirable host cell proteins can be secreted into the upstream cell culture supernatant. Undesirable host cell proteins can also be released during cell lysis. The cells used for upstream cell culture require proteins for growth, transcription, and protein synthesis, and these unrelated proteins are undesirable in a final drug product.

Various aspects of the disclosure are described in further detail in the following subsections.

II. Methods of Recovery Flush

The present disclosure is related to a method of reducing or preventing dilution of a target protein during a recovery flush after a filtration. One aspect of the present disclosure is directed to (i) passing a sample containing the target protein through a filtration assembly at a feed flow rate while the filtration is on and (ii) passing a buffer through the filtration assembly during a recovery flush at a flush flow rate that is less than 300 liters per square meter per hour (LMH), thereby reducing or preventing dilution of the target protein compared to the dilution of a target protein obtained with a flush flow rate of 300 LMH. In another aspect, the present disclosure is related to a method of improving or increasing a concentration of a target protein during a recovery flush after a filtration. One aspect of the present disclosure is directed to (i) passing a sample containing the target protein through a filtration assembly at a feed flow rate while the filtration is on and (ii) passing a flush buffer through the filtration assembly during a recovery flush at a flush flow rate that is less than 300 liters per square meter per hour (LMH), thereby improving the target protein concentration compared to a target protein concentration obtained with a flush flow rate of 300 LMH. In some embodiments, the desired concentration of the target protein is higher than about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL.

A standard approach to purify a protein of interest in a downstream manufacturing process is to concentrate the protein solution to a slightly higher concentration (for example, 20% higher) in order to accommodate the dilution that occurs from the recovery flush. This strategy works well for UF/DF operations at relatively low concentrations of 50 mg/mL prior to formulation. For example, the target protein can be concentrated to 55-60 mg/mL at the filtration stages and diluted down to 50 mg/mL prior to formulation. At protein concentrations of 55-60 mg/mL, the viscosity of some monoclonal antibodies is typically in the range of 2-6 cP at room temperature.

In the case of high protein concentrations, the final concentration and the dilution lead to a vicious circle. When the protein concentration is high, it is desirable to concentrate the target protein at a very high level (i.e., higher than the desired concentration after the filtration) in order to allow the recovery flush to dilute the protein down to the correct concentration, thereby avoiding over-dilution. For example, concentrating protein at a high concentration, e.g., from 150 mg/mL to 170 mg/mL, could take substantial time, leading to additional channel passes through the membrane and potentially impacting product quality. In addition, even after a high concentration is achieved during/after the filtration step, there is a high risk of over-dilution of the product during the recovery flush. This is because in many protein purification processes at scale, a considerable amount of protein can be held outside of the retentate tanks in the tubing or piping. Therefore, due to the high amount of protein held in the tubing or piping, an initial recovery flush might not accumulate the full amount of the recovery product in the collection vessel. This can lead to an additional recovering flushing, which can further dilute the final product concentration. The present methods are designed to prevent or reduce dilution of a target protein during a recovery flush by slowing down the flush flow rate of a flush buffer. Therefore, the present methods allow skipping or avoiding the additional recovery flushing step during the recovery flush process.

In some embodiments, the present disclosure is related to a method of reducing or preventing dilution of a target protein during a recovery flush after a filtration. One aspect of the present disclosure is directed to (i) passing a sample containing the target protein through a filtration assembly at a feed flow rate while the filtration is on and (ii) passing a buffer through the filtration assembly during a recovery flush at a flush flow rate that is less than 300 liters per square meter per hour (LMH), less than about 250 LMH, less than about 200 LMH, less than about 150 LMH, less than about 140 LMH, less than about 130 LMH, less than about 120 LMH, less than about 110 LMH, or less than about 100 LMH, thereby reducing or preventing dilution of the target protein compared to the dilution of a target protein obtained with a flush flow rate of 300 LMH. In another aspect, the present disclosure is related to a method of improving or increasing a concentration of a target protein during a recovery flush after a filtration. One aspect of the present disclosure is directed to (i) passing a sample containing the target protein through a filtration assembly at a feed flow rate while the filtration is on and (ii) passing a flush buffer through the filtration assembly during a recovery flush at a flush flow rate that is less than 300 liters per square meter per hour (LMH), less than about 250 LMH, less than about 200 LMH, less than about 150 LMH, less than about 140 LMH, less than about 130 LMH, less than about 120 LMH, less than about 110 LMH, or less than about 100 LMH, thereby improving the target protein concentration compared to a target protein concentration obtained with a flush flow rate of 300 LMH.

In order to prevent or reduce dilution of the target protein according to the present methods, the flow in the filtration assembly is laminar flow. Laminar flow occurs when a fluid flows in parallel layers, with no disruption between layers. When the Reynolds number is less than about 2,000, flow in a tube is generally laminar. When the Reynolds number is greater than about 4,000, the flow is turbulent. A Reynolds number between 2,000 and 4,000 represents an area of transition between laminar flow and turbulent flow. Therefore, in some embodiments, the Reynold's number ("Re") of the flow in the recovery flush is less than 2000, less than 1900, less than 1800, less than 1700, less than 1600, less than 1500, less than 1400, less than 1300, less than 1200, less than 1100, less than 1000, less than 900, less than 800, less than 700, less than 600, less than 500, less than 400, less than 300, less than 200, less than 100, less than 90, less than 80, less than 70, less than 60, less than 50, less than 40, less than 30, less than 20, less than 10, less than 5, less than 4, less than 3, less than 2, or less than 1, wherein the Re is calculated with the following formula:

$$Re = D\upsilon\rho/\mu, \text{ and}$$

wherein D is the diameter of the channel (m) or equivalent diameter in the case of non-cylindrical flow channel geometries, $\upsilon$ is average velocity (m/s) ($Q/A_c$), $\rho$ is density (kg/m$^3$), and $\mu$ is the viscosity (Pa·s).

In some embodiments, the Reynold's number (Re) of the flow in the recovery flush is between about 1 and about 50, between about 1 and about 45, between about 1 and about 40, between about 1 and about 35, between about 1 and about 30, between about 1 and about 25, between about 1 and about 20, between about 1 and about 15, between about 1 and about 10, between about 1 and about 5, between about 1 and about 4, between about 1 and about 3, between about 2 and about 40, between about 2 and about 9, between about 3 and about 8, between about 4 and about 7, between about 4 and about 6, between about 3 and about 7, between about 3 and about 6, between about 3 and about 5, between about 2 and about 8, between about 2 and about 7, between about 2 and about 6, between about 2 and about 5, between about 3 and about 10, between about 4 and about 6, between about 3 and about 4, or between about 2 and about 3.

In some embodiments, the Reynold's number (Re) of the flow in the recovery flush is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30. In some embodiments, the Reynold's number (Re) of the flow in the recovery flush is about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60. In some embodiments the Re of the flow in the recovery flush is about 3.8.

In certain embodiments, the present disclosure is related to a method of reducing or preventing dilution of a target protein during a recovery flush after a filtration. One aspect of the present disclosure is directed to (i) passing a sample containing the target protein through a filtration assembly at a feed flow rate while the filtration is on and (ii) passing a buffer through the filtration assembly during a recovery flush at a flush flow rate that is less than about 100 liters per square meter per hour (LMH), thereby reducing or preventing dilution of the target protein compared to the dilution of a target protein obtained with a flush flow rate of 300 LMH. In another aspect, the present disclosure is related to a method of improving or increasing a concentration of a target protein during a recovery flush after a filtration. One aspect of the present disclosure is directed to (i) passing a sample containing the target protein through a filtration assembly at a feed flow rate while the filtration is on and (ii) passing a flush buffer through the filtration assembly during a recovery flush at a flush flow rate that is less than about 100 liters per square meter per hour (LMH), thereby improving the target protein concentration compared to a target protein concentration obtained with a flush flow rate of 300 LMH. In some embodiments, the flush flow rate is between about 5 LMH and about 100 LMH, between about 10 LMH and about 100 LMH, between about 10 LMH and about 90 LMH, between about 10 LMH and about 80 LMH, between about 10 LMH and about 70 LMH, between about 10 LMH and about 60 LMH, between about 10 LMH and about 50 LMH, between about 10 LMH and about 40 LMH, between about 10 LMH and about 30 LMH, between about 30 LMH and about 50 LMH, between about 20 LMH and about 100 LMH, between about 20 LMH and about 90 LMH, between about 20 LMH and about 80 LMH, between about 20 LMH and about 70 LMH, between about 20 LMH and about 60 LMH, between about 20 LMH and about 50 LMH, between about 20 LMH and about 40 LMH, between about 30 LMH and about 100 LMH, between about 30 LMH and about 90 LMH, between about 30 LMH and about 80 LMH, between about 30 LMH and about 70 LMH, between about 30 LMH and about 60 LMH, between about 30 LMH and about 50 LMH, between about 30 LMH and about 40 LMH, or between about 20 LMH and about 30 LMH.

In some embodiments, the flush flow rate is at least about 10 LMH, at least about 20 LMH, at least about 30 LMH, at least about 40 LMH, at least about 50 LMH, at least about 60 LMH, at least about 70 LMH, at least about 80 LMH, at least about 90 LMH, or at least about 100 LMH. In some embodiments, the flush flow rate is about 30 LMH.

In certain embodiments, the present disclosure is related to a method of reducing or preventing dilution of a target protein during a recovery flush after a filtration. One aspect of the present disclosure is directed to (i) passing a sample containing the target protein through a filtration assembly at a feed flow rate while the filtration is on and (ii) passing a buffer through the filtration assembly during a recovery flush at a flush flow rate that is less than about 30 liters per square meter per hour (LMH), thereby reducing or preventing dilution of the target protein compared to the dilution of a target protein obtained with a flush flow rate of 300 LMH. In another aspect, the present disclosure is related to a method of improving or increasing a concentration of a target protein during a recovery flush after a filtration. One aspect of the present disclosure is directed to (i) passing a sample containing the target protein through a filtration assembly at a feed flow rate while the filtration is on and (ii) passing a flush buffer through the filtration assembly during a recovery flush at a flush flow rate that is less than about 30 liters per square meter per hour (LMH), thereby improving the target protein concentration compared to a target protein concentration obtained with a flush flow rate of 300 LMH.

In some embodiments, the viscosity of the target protein is at least about 1 centipoise (cP), at least about 2 cP, at least about 3 cP, at least about 4 cP, at least about 5 cP, at least about 6 cP, at least about 7 cP, at least about 8 cP, at least about 9 cP, at least about 10 cP, at least about 11 cP, at least about 12 cP, at least about 13 cP, at least about 14 cP, at least about 15 cP, at least about 16 cP, at least about 17 cP, at least about 18 cP, at least about 19 cP, at least about 20 cP, at least about 21 cP, at least about 22 cP, at least about 23 cP, at least about 24 cP, at least about 25 cP, at least about 26 cP, at least about 27 cP, at least about 28 cP, at least about 29 cP, or at least about 30 cP.

In some embodiments, the present disclosure can be particularly effective in filtering a target protein that has high viscosity. In some embodiments, the viscosity of the target protein is high, and is at least about 20 centipoise (cP), at least about 21 cP, at least about 22 cP, at least about 23 cP, at least about 24 cP, at least about 25 cP, at least about 26 cP, at least about 27 cP, at least about 28 cP, at least about 29 cP, at least about 30 cP, at least about 31 cP, at least about 32 cP, at least about 33 cP, at least about 34 cP, at least about 35 cP, at least about 36 cP, at least about 37 cP, at least about 38 cP, at least about 39 cP, at least about 40 cP, at least about 41 cP, at least about 42 cP, at least about 43 cP, at least about 44 cP, at least about 45 cP, at least about 46 cP, at least about 47 cP, at least about 48 cP, at least about 49 cP, at least about 50 cP, at least about 51 cP, at least about 52 cP, at least about 53 cP, at least about 54 cP, at least about 55 cP, at least about 56 cP, at least about 57 cP, at least about 58 cP, at least about 59 cP, at least about 60 cP, at least about 61 cP, at least about 62 cP, at least about 63 cP, at least about 64 cP, at least about 65 cP, at least about 66 cP, at least about 67 cP, at least about 68 cP, at least about 69 cP, at least about 70 cP, at least about 71 cP, at least about 72 cP, at least about 73 cP, at least about 74 cP, at least about 75 cP, at least about 76 cP, at least about 77 cP, at least about 78 cP, at least about 79 cP, at least about 80 cP, at least about 81 cP, at least about 82 cP, at least about 83 cP, at least about 84 cP, at least about 85 cP, at least about 86 cP, at least about 87 cP, at least about 88 cP, at least about 89 cP, at least about 90 cP, at least about 91 cP, at least about 92 cP, at least about 93 cP, at least about 94 cP, at least about 95 cP, at least about 96 cP, at least about 97 cP, at least about 98 cP, at least about 99 cP, or at least about 100 cP. In some embodiments, the viscosity of the target protein is between about 20 cP and about 100 cP, between about 20 cP and about 90 cP, between 25 cP and about 100 cP, between about 25 cP and about 90 cP, between about 30 cP and about 100 cP, between about 30 cP and about 90 cP, between about 30 cP and about 80 cP, between about 30 cP and about 70 cP, between about 40 cP and about 60 cP. In other embodiments, the viscosity of the target protein is about 10 cP, about 20 cP, about 30 cP, about 40 cP, about 50 cP, about 60 cP, about 70 cP, about 80 cP, about 90 cP, or about 100 cP.

In some embodiments, the viscosity of the target protein is low and is from about 2 cP to about 10 cP, from about 3 cP to about 10 cP, from about 1 cP to about 9 cP, from about 2 cP to about 8 cP, from about 2 cP to about 7 cP, from about 2 cP to about 6 cP, from about 3 cP to about 6 cP, from about 4 cP to about 5 cP, or from about 2 cP to about 5 cP.

There present methods can thus improve the concentration of a target protein after a recovery flush by preventing or reducing dilution of the target protein during the recovery flush. In some embodiments, the concentration of the target protein after the recovery flush is at least about 100 g/L, at least about 110 g/L, at least about 120 g/L, at least about 130 g/L, at least about 140 g/L, at least about 150 g/L, at least about 160 g/L, at least about 170 g/L, at least about 180 g/L, at least about 190 g/L, at least about 200 g/L, at least about 210 g/L, at least about 220 g/L, at least about 230 g/L, at least about 240 g/L, at least about 250 g/L, at least about 260 g/L, at least about 270 g/L, at least about 280 g/L, at least about 290 g/L, or at least about 300 g/L at least about 200 g/L, at least about 210 g/L, at least about 220 g/L, at least about 230 g/L, at least about 240 g/L, at least about 250 g/L, at least about 260 g/L, at least about 270 g/L, at least about 280 g/L, at least about 290 g/L, or at least about 300 g/L before the filtrations.

In some embodiments, the concentration of the target protein after the recovery flush is from about 100 g/L to about 300 g/L, from about 110 g/L to about 250 g/L, from about 120 g/L to about 240 g/L, from about 150 g/L to about 250 g/L, from about 130 g/L to about 260 g/L, from about 140 g/L to about 260 g/L, from about 160 g/L to about 220 g/L, or from about 170 g/L to about 230 g/L.

In some embodiments, the concentration of the target protein after the recovery flush is from about 100 g/L to about 300 g/L, from about 110 g/L to about 300 g/L, from about 110 g/L to about 290 g/L, from about 120 g/L to about 290 g/L, from about 120 g/L to about 280 g/L, from about 130 g/L to about 280 g/L, from about 130 g/L to about 270 g/L, from about 140 g/L to about 270 g/L, from about 140 g/L to about 260 g/L, from about 150 g/L to about 260 g/L, from about 150 g/L to about 250 g/L, from about 160 g/L to about 250 g/L, from about 160 g/L to about 240 g/L, from about 170 g/L to about 240 g/L, from about 170 g/L to about 230 g/L, from about 180 g/L to about 230 g/L, from about 180 g/L to about 220 g/L, from about 190 g/L to about 220 g/L, from about 190 g/L to about 210 g/L, or from about 200 g/L to about 210 g/L.

In some embodiments, the concentration of the target protein after the recovery flush is about 90 g/L, about 100 g/L, about 110 g/L, about 120 g/L, about 130 g/L, about 140 g/L, about 150 g/L, about 160 g/L, about 170 g/L, about 180 g/L, about 190 g/L, about 200 g/L, about 210 g/L, about 220 g/L, about 230 g/L, about 240 g/L, about 250 g/L, about 260 g/L, about 270 g/L, about 280 g/L, about 290 g/L, or about 300 g/L.

In some embodiments, the yield of the target protein after the recovery flush according to the present methods is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% compared to the concentration of the target protein prior to the recovery flush process.

In some embodiments, the yield of the target protein after the recovery flush according to the present methods is increased by at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, or at least about 40%, compared to a yield of the target protein obtained after a recovery flush with a flow rate of 300 LMH. In some embodiments, the passing in (i) is at a feed flow rate higher than the flush flow rate in (ii).

According to the present methods, the target protein is passed through the filtration assembly while the filtration is on. The rate of flow in a tangential flow filtration (TFF) step wherein a feed containing a target protein is referred to herein as a feed flow rate as opposed to a flush flow rate. The tangential flow of the feed prevents particles trapped on the surface of the filter to accumulate and therefore interfere with filtration. During an ultrafiltration concentration step, the feed flow to the ultrafiltration membrane cassette provides the necessary transmembrane pressure (TMP) and crossflow flux for the concentration and buffer exchange.

In the present disclosure, the feed flow rate is higher than the flush flow rate. In some embodiments, the feed flow rate is at least 200 LMH, at least 210 LMH, at least 220 LMH, at least 230 LMH, at least 240 LMH, at least 250 LMH, at least 260 LMH, at least 270 LMH, at least 280 LMH, at least 290 LMH, at least 300 LMH, at least 310 LMH, at least 320 LMH, at least 330 LMH, at least 340 LMH, at least 350 LMH, at least 360 LMH, at least 370 LMH, at least 380 LMH, at least 390 LMH, at least 400 LMH, at least 410 LMH, at least 420 LMH, at least 430 LMH, at least 440 LMH, at least 450 LMH, at least 460 LMH, at least 470 LMH, at least 480 LMH, at least 490 LMH, or at least 500 LMH, wherein the flush flow rate is lower than the feed flow rate, e.g., lower than 100 LMH.

In some embodiments, the feed flow rate is between 200 LMH and 500 LMH, between 200 LMH and 450 LMH, between 250 LMH and 450 LMH, 450 LMH, between 300 LMH and 450 LMH, between 300 LMH and 400 LMH, or between 300 LMH and 350 LMH. In some embodiments, the feed flow rate is about 300 LMH.

According to the present methods, a filtration assembly is used to carry out the filtration of the protein of interest. A filtration assembly generally comprises elements such as a filter holder, a filtration cassette, and a port for the filtrate to flow. The filtration cassette is the element of the assembly that usually holds the membrane filter that is used for separation and purification of biomolecules. A filtration membrane is used to purify the target protein of interest. In some embodiments, a filtration membrane is used to retain cells, cell debris, organelles, and other components while allowing proteins and smaller solutes to pass into the filtrate. In some embodiments, the filtration assembly comprises a membrane. In other embodiments, the membrane useful for the filtration assembly membrane is derived from polyvinylidene fluoride (PVDF), polysulfone, polyethersulfone, polyarylsulfone, regenerated cellulose, polyamide, polypropylene, polyethylene, polytetrafluoroethylene, cellulose acetate, polyacrylonitrile, vinyl copolymer, polyamides (such as "Nylon 6" or Nylon 66") polycarbonate, PFA, or any combination thereof.

Methods according to the present disclosure include use of a flush buffer during a recovery flush to recover protein that is held outside of the collection vessels in the tubing, piping or other "hold-up" areas. A recovery flush is necessary to recover a larger amount of protein product in the collection vessel or other container used to collect the purified protein product, as not all of the purified protein reaches the collection vessel during the initial purification run. In some instances, protein purification and concentration to high levels may lead to unwanted protein aggregation. Modification of the pH, salt content, or other components of the buffer may be necessary to prevent protein aggregation or other unwanted effects during the purification and concentration process. In some embodiments, the flush buffer comprises an organic or inorganic acid or salt thereof. In some embodiments, the organic or inorganic acid is citrate (e.g., monosodium citrate-disodium citrate mixture, citric acid-trisodium citrate mixture, citric acid-monosodium citrate mixture, etc.), succinate (e.g., succinic acid-monosodium succinate mixture, succinic acid-sodium hydroxide mixture, succinic acid-disodium succinate mixture, etc.), tartrate (e.g., tartaric acid-sodium tartrate mixture, tartaric acid-potassium tartrate mixture, tartaric acid-sodium hydroxide mixture, etc.), fumarate (e.g., fumaric acid-monosodium fumarate mixture, fumaric acid-disodium fumarate mixture, monosodium fumarate-disodium fumarate mixture, etc.), gluconate (e.g., gluconic acid-sodium glyconate mixture, gluconic acid-sodium hydroxide mixture, gluconic acid-potassium glyuconate mixture, etc.), oxalate (e.g., oxalic acid-sodium oxalate mixture, oxalic acid-sodium hydroxide mixture, oxalic acid-potassium oxalate mixture, etc.), lactate (e.g., lactic acid-sodium lactate mixture, lactic acid-sodium hydroxide mixture, lactic acid-potassium lactate mixture, etc.) acetate (e.g., acetic acid-sodium acetate mixture, acetic acid-sodium hydroxide mixture, etc.), trimethylamine salt (e.g., Tris), phosphate, or histidine. In some embodiments, the flush buffer comprises histidine. In some embodiments, the flush buffer comprises a sugar. In some embodiments, the sugar is sucrose, trehalose, mannitol, xylitol, erythritol, lactose, glucose, powdered sugar, or pullulan. In some embodiments, the flush buffer comprises 20 mM histidine and 250 mM sucrose.

According to the methods of the present disclosure, a filtration buffer is used during the process of passing a sample containing the target protein through a filtration assembly at a feed flow rate while the filtration is on. The filtration buffer is essential in protecting downstream chromatography and filtration equipment, and is used during the protein purification and concentration process. The filtration buffer differs from the flush buffer in that the flush buffer is used during flush recovery, which follows the protein purification and concentration process. In some embodiments, the components in the filtration buffer is the same as those in the flush buffer. In other embodiments, the components in the filtration buffer is different from those in the flush buffer.

Protein purification and concentration to high levels may lead to unwanted protein aggregation. Modification of the pH, salt content, or other components of the buffer may be necessary to prevent protein aggregation or other unwanted effects during the purification and concentration process. In some embodiments, the filtration buffer comprises an organic and inorganic acid or salt thereof. In some embodiments, the organic or inorganic acid is citrate (e.g., monosodium citrate-disodium citrate mixture, citric acid-trisodium citrate mixture, citric acid-monosodium citrate mixture, etc.), succinate (e.g., succinic acid-monosodium succinate mixture, succinic acid-sodium hydroxide mixture, succinic acid-disodium succinate mixture, etc.), tartrate (e.g., tartaric acid-sodium tartrate mixture, tartaric acid-potassium tartrate mixture, tartaric acid-sodium hydroxide mixture, etc.), fumarate (e.g., fumaric acid-monosodium fumarate mixture, fumaric acid-disodium fumarate mixture, monosodium fumarate-disodium fumarate mixture, etc.), gluconate (e.g., gluconic acid-sodium glyconate mixture, gluconic acid-sodium hydroxide mixture, gluconic acid-potassium glyuconate mixture, etc.), oxalate (e.g., oxalic acid-sodium oxalate mixture, oxalic acid-sodium hydroxide mixture, oxalic acid-potassium oxalate mixture, etc.), lactate (e.g., lactic acid-sodium lactate mixture, lactic acid-sodium hydroxide mixture, lactic acid-potassium lactate mixture, etc.) acetate (e.g., acetic acid-sodium acetate mixture, acetic acid-sodium hydroxide mixture, etc.), trimethylamine salt (e.g., Tris), phosphate, or histidine.

In some embodiments, the filtration buffer comprises a sugar. In some embodiments, the sugar is sucrose, trehalose, mannitol, xylitol, erythritol, lactose, glucose, powdered sugar, or pullulan. In some embodiments, the flush buffer and/or the filtration buffer is at a pH of about 4, about 4.5, about 5, about 5.5, about 6, about 6.5, about 7, about 7.5, about 8, about 8.5, about 9, or about 9.5.

According to the methods of the present invention, a sample containing a protein of interest is first passed through a filtration assembly and then subjected to a recovery flush. In some embodiments, the sample may have already been subjected to previous purification activities directly upstream of the filtration and recovery flush step, such as virus filtration, anion-exchange chromatography (AEX), cation-exchange chromatography (CEX), depth filtration, acid treatment, or protein A chromatography. The sample that is subjected to purification and filtration can be derived from sources such as cell cultures, cell lysates, or clarified bulk (e.g., clarified cell culture supernatant). In some embodiments, the sample is selected from the group consisting of a pure protein sample, a clarified bulk protein sample, a cell culture sample, and any combination thereof. In some embodiments, the cell culture sample is derived from cell culture media comprising mammalian cells. In some embodiments, the mammalian cells are selected from Chinese hamster ovary (CHO) cells, HEK293 cells, mouse myeloma (NS0), baby hamster kidney cells (BHK), monkey kidney fibroblast cells (COS-7), Madin-Darby bovine kidney cells (MDBK) or any combination thereof.

The target protein useful for the present methods is any protein, polypeptide, or peptide, either naturally occurring or recombinantly produced. In some embodiments, the target protein has high viscosity. In some embodiments, the target protein is a protein with a high molecular weight (e.g., 100 kDa to 500 kDa). In other embodiments, the target protein is a protein with a low molecular weight. In other embodiments, the target protein has a molecular weight of at least about 10 kDa, at least about 20 kDa, at least about 30 kDa, at least about 40 kDa, at least about 50 kDa, at least about 60 kDa, at least about 70 kDa, at least about 80 kDa, at least about 90 kDa, at least about 100 kDa, at least about 110 kDa, at least about 120 kDa, at least about 130 kDa, at least about 140 kDa, at least about 150 kDa, at least about 160 kDa, at least about 170 kDa, at least about 180 kDa, at least about 190 kDa, or at least about 200 kDa, and up to 400 kDa or 500 kDa.

In some embodiments, the target protein comprises an antibody or a fusion protein. In some embodiments, the target protein comprises an antibody. In some embodiments, the antibody is an isotype selected from IgM, IgA, IgE, IgD, and IgG. In some embodiments, the IgG antibody is selected from IgG1, IgG2, IgG3, and IgG4. The present methods can be applicable to any antibodies that specifically bind to an antigen. In some embodiments, the antibody is an anti-GITR antibody, an anti-CXCR4 antibody, an anti-CD73 antibody, an anti-TIGIT antibody, an anti-OX40 antibody, an anti-LAG3 antibody, an anti-CSF1R antibody, or an anti-IL8 antibody.

In some embodiments, the target protein comprises an enzyme, a hormone, a cytokine, a cell surface receptor, a protease, a cytokine receptor, or any combination thereof. In some embodiments, the target protein is a fusion protein. In some embodiments, the fusion protein is fused to a heterologous moiety. In some embodiments, the heterologous moiety is a half-life extending moiety. In some embodiments, the heterologous moiety comprises albumin, an immunoglobulin constant region or a portion thereof, an immunoglobulin-binding polypeptide, an immunoglobulin G (IgG), albumin-binding polypeptide (ABP), a PASylation moiety, a HESylation moiety, XTEN, a PEGylation moiety, an Fc region, and any combination thereof. In some embodiments, the half-life extending moiety comprises a non-polypeptide moiety. In some embodiments, the half-life extending moiety comprises a polypeptide. In some embodiments, the half-life extending moiety comprises an Fc. In certain embodiments, a fusion protein for the present disclosure comprises an amino acid substitution to an immunoglobulin constant region or a portion thereof (e.g., Fc variants), which alters the antigen-independent effector functions of the Ig constant region, in particular the circulating half-life of the protein.

EXAMPLES

Example 1

Evaluation of Scale-Down Design

Figure 1:
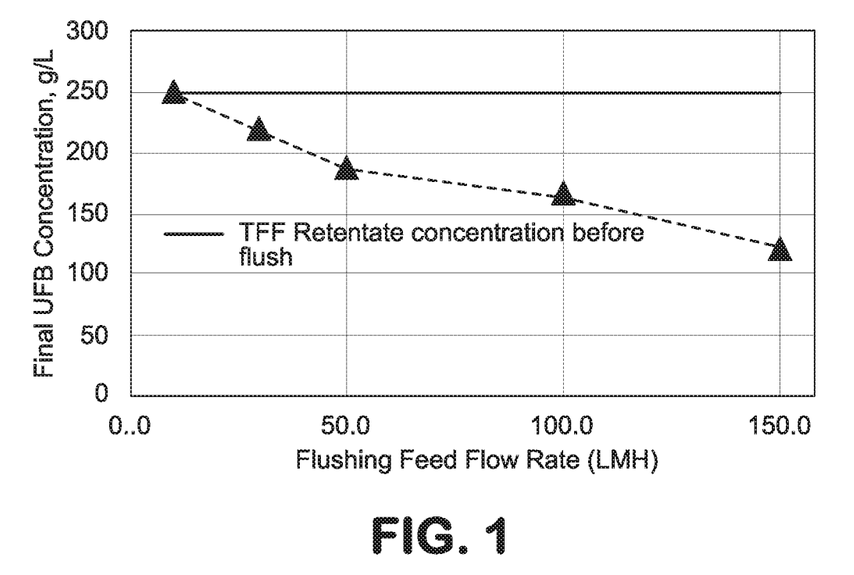
FIG. 1 (FIG. 1) shows data generated from a scaled-down process using size 16 feed tubing (176 $cm^2$ membrane area). After concentration of the TFF retentate above the target concentration before the recovery flush, a number of different recovery flush flow-rates were tested. As can be seen in FIG. 1, higher recovery flush flow-rates lead to greater dilution of the concentrated TFF retentate.

In order to evaluate potential recovery flush processes, a scaled-down model was designed to analyze changes in tubing size. This scaled down model used a 176 cm$^2$ membrane area, and was first tested using size 16 tubing. Various tubings used in the modeling are described in Table 1. A starting protein concentration of 250 g/L was used and various flushing feed flow rates were tested. This data are represented in FIG. 1. A higher flushing feed flow rate leads to a lower final protein concentration, and therefore lower flushing flow-rates would be desirable as seen in FIG. 1.

TABLE 1

| | Scale Dependent Tubing | | |
|---|---|---|---|
| Parameter | Size 16 | CM150 | DCM Allegro |
| Internal Diameter (mm) | 3.1 | 9.6 | 12.7 |
| Internal Diameter (m) | $3.1 \times 10^{-3}$ | $9.6 \times 10^{-3}$ | $1.3 \times 10^{-2}$ |
| Area of Cross Section (m$^2$) | $7.55 \times 10^{-6}$ | $7.24 \times 10^{-5}$ | $1.27 \times 10^{-4}$ |

Figure 2:
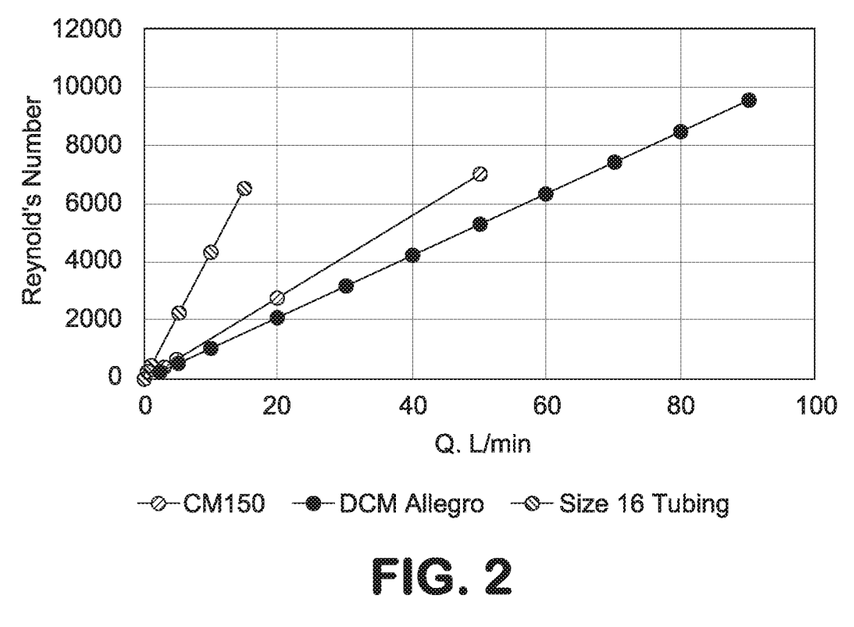
FIG. 2 (FIG. 2) shows a comparison of calculated Reynold's Numbers using tubing with various cross-sectional areas. The cross-sectional areas are displayed in Table 1.

The flow rate parameter's effect on the Reynold's Number was explored using a mixture with a fixed viscosity and density, and is detailed in FIG. 2. The mixture had a viscosity of 17 cP and a density of 1.08 g/cm$^3$, and a fixed flow rate of 30 liters/M$^2$/hour was used. Due to differences in the cross-section of the various tubing used, the specific flow rates for each tubing had to be adjusted. A flow rate of 0.03 L/min was used for the CM150 system, and a flow rate of 0.04 L/min was used for DCM.

Figure 3:
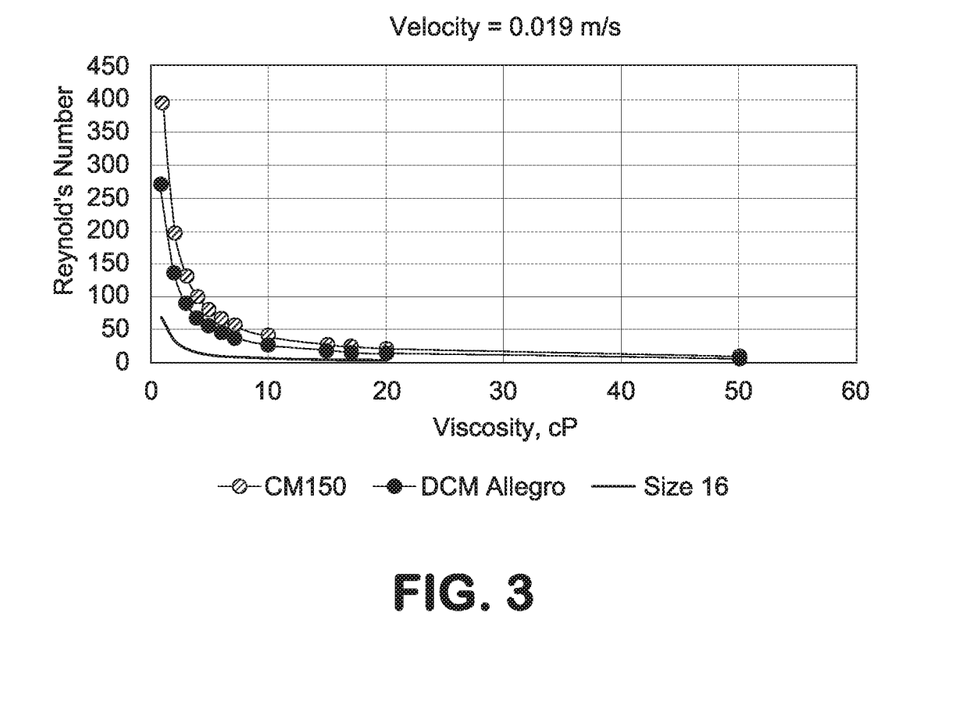
FIG. 3 (FIG. 3) shows a comparison of calculated Reynold's Numbers as compared to the viscosity of a fluid traveling at fixed velocity through tubes of various cross sectional-areas.

The effect of viscosity on the Reynold's Number was also evaluated using a fixed flow rate of 0.019 m/s. These data are summarized in FIG. 3. Higher viscosities led to higher calculated Reynold's Numbers for each of the tubing types.

Example 2

Evaluation of Flush Strategy Using Various Monoclonal Antibodies

Three monoclonal antibodies (A, B, and C) were evaluated using the designed flush process. Data collected from the antibody A flush process are detailed in Table 2. These data include flush flux (LMH), Reynold's Number (Re), retentate concentration, purified drug substance concentration, yield, expected yield, and flush volume. After evaluation of a scale-down flush process, the approach was also validated at the CM150 Tangential Flow Filtration (TFF) scale for monoclonal antibody A. In all instances, the flow rate was set to a flux of 30 Liters/M²/Hour. Accounting for the cross-section of the tubing used in the CM150 system, this corresponds to a Reynold's Number of 265 in the CM150 system. Additional scale down and CM150 TFF data were generated for monoclonal antibodies B and C, and these date are presented in Table 2 and Table 3, respectively.

TABLE 2

Data For Monoclonal Antibody A

| | Flush Flux (LMH) | Re | Retentate (g/L) | PDS (g/L) | Yield | Expected Yield | Volume |
|---|---|---|---|---|---|---|---|
| Scale-down Run | 30 | 3.8 | 183 | 174 | 98% | 75.4% | 1x |
| Confirmation Run | 30 | 3.8 | 158 | 150 | 91% | 75.6% | 1x |
| Tox Run using CM150 (Run 1) | 30 | 265 | 163 | 157 | 97% | 96.5% | 1x |
| CM 150 (Run 2) | 30 | 265 | 153 | 150 | 100 | 96.3% | 1.2x |
| CM 150 (Run 3) | 30 | 265 | 161 | 155 | 102.5% | 97.4% | 1.2x |

TABLE 3

30 liters/M²/hour Recovery Flush Of Monoclonal Antibody B

| Run ID | System | TFF Retentate Concentration (g/L) | PDS Concentration (g/L) | UF/DF Yield (%) | Expected Yield |
|---|---|---|---|---|---|
| Development Run | Lab Scale | 211 | 188 | 95 | 82.3% |
| Scale Up Run | CM150 | 187 | 178 | 105 | 96.0% |

TABLE 3

30 liters/M²/hour Recovery Flush Of Monoclonal Antibody C

| Run ID | System | TFF Retentate Concentration (g/L) | PDS Concentration (g/L) | UF/DF Yield (%) | Expected Yield |
|---|---|---|---|---|---|
| Development Run 1 | Lab Scale | 129 | 123 | 96 | 75% |
| Development Run 2 | Lab Scale | 154 | 140 | 92 | 80.5% |

It is to be appreciated that the Detailed Description section, and not the Summary and Abstract sections, is intended to be used to interpret the claims. The Summary and Abstract sections may set forth one or more but not all exemplary aspects of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the invention that others can, by applying knowledge within the skill of the art, readily modify and/or adapt for various applications such specific aspects, without undue experimentation, without departing from the general concept of the present invention. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary aspects, but should be defined only in accordance with the following claims and their equivalents.

We claim:

1. A method of reducing or preventing dilution of a target protein during a recovery flush after a filtration comprising (i) passing a sample containing the target protein through a filtration assembly at a feed flow rate while the filtration is on and (ii) passing a buffer through the filtration assembly during a recovery flush at a flush flow rate that is between about 10 and about 40 liters per square meter per hour (LMH), thereby reducing or preventing dilution of the target protein compared to the dilution of a target protein obtained with a flush flow rate of 300 LMH, wherein the Reynold's number ("Re") of the flow in the recovery flush is between about 1 and about 50, wherein the Re is calculated with the following formula:

$$Re = D\upsilon\rho/\mu, \text{ and}$$

wherein D is the diameter of the channel (m) or equivalent diameter in the case of non-cylindrical flow channel geometries, $\upsilon$ is average velocity (m/s) ($Q/A_c$), $\rho$ is density (kg/m³), and $\mu$ is the viscosity (Pa·s).

2. A method of improving or increasing a concentration of a target protein during a recovery flush after a filtration comprising (i) passing a sample containing the target protein through a filtration assembly at a feed flow rate while the filtration is on and (ii) passing a flush buffer through the filtration assembly during a recovery flush at a flush flow rate that is between about 10 and about 40 liters per square meter per hour (LMH), thereby improving the target protein concentration compared to a target protein concentration obtained with a flush flow rate of 300 LMH, wherein the Reynold's number ("Re") of the flow in the recovery flush is between about 1 and about 50, wherein the Re is calculated with the following formula:

$$Re = D\upsilon\rho/\mu, \text{ and}$$

wherein D is the diameter of the channel (m) or equivalent diameter in the case of non-cylindrical flow channel geometries, $\upsilon$ is average velocity (m/s) ($Q/A_c$), $\rho$ is density (kg/m$^3$), and $\mu$ is the viscosity (Pa·s).

3. The method of claim 2, wherein the Re of the flow in the recovery flush is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30.

4. The method of claim 2, wherein the Re of the flow in the recovery flush is about 3.8.

5. The method of claim 2, wherein the flush flow rate is about 30 LMH.

6. The method of claim 2, wherein the viscosity of the target protein is at least about 1 centipoise (cP).

7. The method of method of claim 2, wherein the viscosity of the target protein is at least about 20 centipoise (cP).

8. The method of claim 2, wherein the viscosity of the target protein is from about 2 cP to about 10 cP.

9. The method of claim 2, wherein the concentration of the target protein after the recovery flush is at least about 100 g/L before the filtrations.

10. The method of claim 9, wherein the concentration of the target protein after the recovery flush is from about 100 g/L to about 300 g/L, from about 110 g/L to about 250 g/L, from about 120 g/L to about 240 g/L, from about 150 g/L to about 250 g/L, from about 130 g/L to about 260 g/L, from about 140 g/L to about 260 g/L, from about 160 g/L to about 220 g/L, or from about 170 g/L to about 230 g/L.

11. The method of claim 2, wherein the yield of the target protein after the recovery flush is at least 90% compared to the concentration of the target protein prior to the recovery flush process consisting of (i) and (ii).

12. The method of claim 2, wherein the yield of the target protein after the recovery flush is increased by at least 1% compared to a yield of the target protein obtained after a recovery flush with a flow rate of 300 LMH.

13. The method of claim 2, wherein the passing in (i) is at a feed flow rate higher than the flush flow rate in (ii).

14. The method of claim 13, wherein the feed flow rate is at least 200 LMH.

15. The method of claim 13, wherein the feed flow rate is between 200 LMH and 500 LMH.

16. The method of claim 13, wherein the feed flow rate is about 300 LMH.

17. The method of claim 2, wherein the filtration assembly comprises a membrane, which is derived from polyvinylidene fluoride (PVDF), polysulfone, polyethersulfone, polyarylsulfone, regenerated cellulose, polyamide, polypropylene, polyethylene, polytetrafluoroethylene, cellulose acetate, polyacrylonitrile, vinyl copolymer, polyamides polycarbonate, PFA, or any combination thereof.

18. The method of claim 2, wherein the flush buffer comprises an organic and inorganic acid or salt thereof.

19. The method of claim 18, wherein the organic or inorganic acid is citrate (e.g., monosodium citrate-disodium citrate mixture, citric acid-trisodium citrate mixture, citric acid-monosodium citrate mixture, etc.), succinate (e.g., succinic acid-monosodium succinate mixture, succinic acid-sodium hydroxide mixture, succinic acid-disodium succinate mixture, etc.), tartrate (e.g., tartaric acid-sodium tartrate mixture, tartaric acid-potassium tartrate mixture, tartaric acid-sodium hydroxide mixture, etc.), fumarate (e.g., fumaric acid-monosodium fumarate mixture, fumaric acid-disodium fumarate mixture, monosodium fumarate-disodium fumarate mixture, etc.), gluconate (e.g., gluconic acid-sodium glyconate mixture, gluconic acid-sodium hydroxide mixture, gluconic acid-potassium glyconate mixture, etc.), oxalate (e.g., oxalic acid-sodium oxalate mixture, oxalic acid-sodium hydroxide mixture, oxalic acid-potassium oxalate mixture, etc.), lactate (e.g., lactic acid-sodium lactate mixture, lactic acid-sodium hydroxide mixture, lactic acid-potassium lactate mixture, etc.) acetate (e.g., acetic acid-sodium acetate mixture, acetic acid-sodium hydroxide mixture, etc.), trimethylamine salt (e.g., Tris), phosphate, or histidine.

20. The method of claim 18, wherein the flush buffer comprises histidine.

21. The method of claim 2, wherein the flush buffer comprises a sugar.

22. The method of claim 21, wherein the sugar is sucrose, trehalose, mannitol, xylitol, erythritol, lactose, glucose, powdered sugar, or pullulan.

23. The method of claim 2, wherein the flush buffer comprises about 20 mM histidine and about 250 mM sucrose.

24. The method of claim 2, wherein a filtration buffer is used during (i).

25. The method of claim 24, wherein the filtration buffer is the same as the flush buffer.

26. The method of claim 24, wherein the filtration buffer is different from the flush buffer.

27. The method of claim 24, wherein the filtration buffer comprises an organic and inorganic acid or salt thereof.

28. The method of claim 27, wherein the organic or inorganic acid is citrate (e.g., monosodium citrate-disodium citrate mixture, citric acid-trisodium citrate mixture, citric acid-monosodium citrate mixture, etc.), succinate (e.g., succinic acid-monosodium succinate mixture, succinic acid-sodium hydroxide mixture, succinic acid-disodium succinate mixture, etc.), tartrate (e.g., tartaric acid-sodium tartrate mixture, tartaric acid-potassium tartrate mixture, tartaric acid-sodium hydroxide mixture, etc.), fumarate (e.g., fumaric acid-monosodium fumarate mixture, fumaric acid-disodium fumarate mixture, monosodium fumarate-disodium fumarate mixture, etc.), gluconate (e.g., gluconic acid-sodium glyconate mixture, gluconic acid-sodium hydroxide mixture, gluconic acid-potassium glyuconate mixture, etc.), oxalate (e.g., oxalic acid-sodium oxalate mixture, oxalic acid-sodium hydroxide mixture, oxalic acid-potassium oxalate mixture, etc.), lactate (e.g., lactic acid-sodium lactate mixture, lactic acid-sodium hydroxide mixture, lactic acid-potassium lactate mixture, etc.) acetate (e.g., acetic acid-sodium acetate mixture, acetic acid-sodium hydroxide mixture, etc.), trimethylamine salt (e.g., Tris), phosphate, or histidine.

29. The method of claim 24, wherein the filtration buffer comprises a sugar.

30. The method of claim 29, wherein the sugar is sucrose, trehalose, mannitol, xylitol, erythritol, lactose, glucose, powdered sugar, or pullulan.

31. The method of claim 24, wherein the flush buffer and/or the filtration buffer is at a pH of about 4, about 4.5, about 5, about 5.5, about 6, about 6.5, about 7, about 7.5, about 8, about 8.5, about 9, or about 9.5.

32. The method of claim 2, wherein the sample comprises a pure protein sample, a clarified bulk protein sample, a cell culture sample, or any combination thereof.

33. The method of claim 1, wherein the Re of the flow in the recovery flush is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30.

34. The method of claim 1, wherein the Re of the flow in the recovery flush is about 3.8.

35. The method of claim 1, wherein the flush flow rate is about 30 LMH.

\* \* \* \* \*